(12) United States Patent
Sendai

(10) Patent No.: US 7,668,287 B2
(45) Date of Patent: Feb. 23, 2010

(54) RADIATION CT APPARATUS

(75) Inventor: Tomonari Sendai, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/405,855

(22) Filed: Mar. 17, 2009

(65) Prior Publication Data

US 2009/0232273 A1    Sep. 17, 2009

(30) Foreign Application Priority Data

Mar. 17, 2008    (JP) .............................. 2008-066992

(51) Int. Cl.
*A61B 6/00*    (2006.01)
(52) U.S. Cl. .......................................... 378/15; 378/37
(58) Field of Classification Search ............... 378/4–20, 378/37
See application file for complete search history.

(56) References Cited

U.S. PATENT DOCUMENTS

2006/0094950 A1    5/2006    Ning
2007/0064867 A1    3/2007    Hansen et al.

*Primary Examiner*—Courtney Thomas
(74) *Attorney, Agent, or Firm*—Sughrue Mion, PLLC

(57) ABSTRACT

An imaging section includes a radiation source that emits radiation, a detecting panel for detecting the radiation, and a rotating section for integrally rotating the radiation source and the detecting panel about a rotating axis. The radiation source and the detecting panel face each other with the rotating axis that passes though a predetermined position interposed therebetween. The imaging section sequentially images a subject placed at the predetermined position while rotating the radiation source and the detecting panel about the rotating axis, and image signals are read out for each imaging operation. A control section refers to a necessary readout region set by a setting section and controls a readout switching means such that image signals recorded in detection pixels within the necessary readout region are read out by a normal readout section, and image signals recorded in other detection pixels are read out by a high speed readout section.

20 Claims, 4 Drawing Sheets

RADIATION CT APPARATUS

BACKGROUND OF THE INVENTION

1. Field of the Invention

The present invention is related to a radiation CT apparatus. More specifically, the present invention is related to a radiation CT apparatus that obtains radiation images of subjects by sequential imaging.

2. Description of the Related Art

There are known bed type radiation CT apparatuses which are employed to perform radiation imaging of breasts (refer to U.S. Patent Application Publication Nos. 20060094950 and 20070064867). In these radiation CT (Computed Tomography) apparatuses, a patient lays face down on a support base, and the patient's breast is fitted through an opening which is formed in the support base. Radiation imaging is performed with the breast which is positioned below the support base as the subject.

The above radiation CT apparatuses are equipped with a radiation source that emits radiation, and a detecting panel that detects the emitted radiation. When performing radiation imaging, the radiation source and the detecting panel are provided such that they face each other with a breast positioned below a bed interposed therebetween. Radiation imaging of the breast is sequentially performed while integrally rotating the radiation source and the detecting panel about an axis of rotation that passes vertically through the breast. Thereby, a plurality of radiation images of the breast are obtained, which are thereafter reconstituted to generate a radiation CT image.

When radiation is irradiated onto the detecting panel during radiation imaging, electrical image signals that represent a radiation image of the subject are accumulated in each detection pixel that constitutes the detecting panel. When reading out the radiation image recorded in the detecting panel, image signals are read out from all of the detection pixels of the detecting panel. For this reason, sequential radiation imaging is performed by these radiation CT apparatuses such that a radiation imaging operation is performed after all of the image signals which were accumulated by a preceding radiation imaging operation have been read out from all of the detection pixels of the detecting panel.

In addition, the distance from the axis of rotation to the radiation source and the distance from the axis of rotation to the detecting panel are fixed in the above radiation CT apparatuses. That is, these radiation CT apparatuses are configured such that the imaging magnification rate of the radiation images of the subject, which are recorded in the detecting panel, is constant.

Breasts, which are the subjects of radiation images, vary in size. Radiation CT apparatuses are equipped with detecting panels of a size that enables radiation imaging of extremely large breasts. In the case that radiation imaging of a smaller breast is performed using these detecting panels which are large enough to image extremely large breasts, the ratio of the area of the detecting panel in which a radiation image of the breast is formed becomes small. That is, the image signals recorded in the detecting panel by radiation, which is irradiated thereon during radiation imaging of the breast, include a large amount of unnecessary image signals of regions, so called blank pixel regions, in which radiation has not passed through the breast.

However, readout of image signals from detecting panels is performed by reading out image signals from all of the detection pixels that constitute the detecting panels. That is, effective image signals that represent an image of the breast and unnecessary image signals that represent the blank pixel portions are read out without being distinguished from each other. For this reason, the ratio of unnecessary image signals which are read out from the detecting panel when radiation imaging of a smaller breast is performed. The utilization efficiency of the detecting panel deteriorates compared to a case in which radiation imaging of a large breast is performed. In addition, the readout efficiency of image signals also deteriorates.

In the case that radiation images of a breast are obtained sequentially, a single detecting panel is used to perform imaging and readout repeatedly. Therefore, the effect of deteriorated readout efficiency becomes great.

Note that this problem is not limited to cases in which breasts are imaged, but is common to all types of radiation imaging by radiation CT apparatuses.

SUMMARY OF THE INVENTION

The present invention has been developed in view of the foregoing circumstances. It is an object of the present invention to provide a radiation CT apparatus which is capable of increasing readout efficiency when reading out radiation images which are recorded by radiation imaging.

A first radiation CT apparatus of the present invention comprises:

an imaging portion constituted by a radiation source that emits radiation in a conical manner, a detecting panel for detecting the radiation, the radiation source and the detecting panel being provided to face each other with an axis of rotation that passes though a predetermined position sandwiched therebetween, and rotating means for integrally rotating the radiation source and the detecting panel about the axis of rotation; and readout means for reading out image signals which are recorded in detection pixels that constitute the detecting panel;

the imaging portion continuously imaging a subject which is placed at the predetermined position while rotating the radiation source and the detecting panel about the axis of rotation, and the image signals being read out for each imaging operation by the readout means; and is characterized by further comprising:

setting means for setting a necessary readout region within the detecting panel; and control means for referring to the results of setting by the setting means and controlling the readout means such that only image signals recorded in detection pixels within the necessary readout region are read out.

A second radiation CT apparatus of the present invention comprises:

an imaging portion constituted by a radiation source that emits radiation in a conical manner, a detecting panel for detecting the radiation, the radiation source and the detecting panel being provided to face each other with an axis of rotation that passes though a predetermined position sandwiched therebetween, and rotating means for integrally rotating the radiation source and the detecting panel about the axis of rotation; and readout means for reading out image signals which are recorded in detection pixels that constitute the detecting panel;

the imaging portion continuously imaging a subject which is placed at the predetermined position while rotating the radiation source and the detecting panel about the axis of rotation, and the image signals being read out for each imaging operation by the readout means; and is characterized by further comprising:

setting means for setting a necessary readout region within the detecting panel;

normal readout means for reading out image signals recorded in the detection pixels that constitute the detecting panel at a normal speed;

high speed readout means for reading out image signals recorded in the detection pixels that constitute the detecting panel at a high speed;

readout switching means for switching between readout of the image signals by the normal readout means and readout of the image signals by the high speed readout means; and control means for referring to the results of setting by the setting means and controlling the readout switching means such that image signals recorded in detection pixels within the necessary readout region are read out by the normal readout means, and image signals recorded in detection pixels other than those within the necessary readout region are read out by the high speed readout means.

The high speed readout means may perform a binning process on image signals recorded in detection pixels other than those within the necessary readout region prior to reading out the image signals. Alternatively, the high speed readout means may discard image signals recorded in detection pixels other than those within the necessary readout region via a clear line provided to remove electric signals which are accumulated in the detection pixels of the detecting panel.

As a further alternative, the high speed readout means may read out image signals recorded in detection pixels other than those within the necessary readout region at a higher readout clock signal frequency, which regulates the timing of the readout process.

The setting section may determine the necessary readout region according to the open state of a irradiation field aperture that determines the radiation field of the radiation during imaging.

The radiation source may emit radiation at a normal dosage, and radiation at a lower dosage than the normal dosage; and the setting section may determine the necessary readout region employing a radiation image which is recorded on the detecting panel by imaging with the lower dosage radiation.

The first and second radiation CT apparatuses of the present invention may further comprise:

a visible light imaging means for performing visible light imaging that converts the propagating region of radiation, which is emitted from the radiation source and detected by the detecting panel, to the visible range; and wherein the setting section sets the necessary readout region employing visible light images, which are obtained by visible light imaging by the visible light imaging means.

The setting section may set the necessary readout region for each imaging operation of the sequential imaging operations performed by the imaging section. Further, the setting section may set the necessary readout region for each imaging operation of the sequential imaging operations performed by the imaging section, employing a radiation image obtained by a previous radiation imaging operation. In this case, the previous radiation imaging operation may be the immediately preceding radiation imaging operation.

The necessary readout region may be a region within the detecting panel at which a radiation image of the subject is formed by the radiation imaging operation. The necessary readout region may be a region within the detecting panel at which a radiation image that represents a region of interest within the subject is formed by the radiation imaging operation.

The subject may be a breast. The region of interest may be a diseased area.

Here, the "predetermined position" is a position at which the subject of radiation imaging is placed.

The phrase "integrally rotating the radiation source and the detecting panel about the axis of rotation" refers to a state in which the radiation source and the detecting panel are rotated about the axis of rotation, without changing the relative positional relationship among the radiation source, the detecting panel, and the axis of rotation.

The speed at which the image signals are read out corresponds to the amount of time between readout of image signals from a detection pixel to initiation of readout of image signals from a next detection pixel. The higher the readout speed of image signals from a detection pixel is, the amount of readout time for the detection pixel becomes shorter.

According to the first radiation CT apparatus of the present invention, the results of setting by the setting means are referred to and the readout means is controlled such that only image signals recorded in detection pixels within the necessary readout region are read out. According to the second radiation CT apparatus of the present invention, the results of setting by the setting means are referred to and the readout switching means is controlled such that image signals recorded in detection pixels within the necessary readout region are read out by the normal readout means, and image signals recorded in detection pixels other than those within the necessary readout region are read out by the high speed readout means. Therefore, the time required to read out image signals from the detecting panels can be shortened. Thereby, the readout efficiency during readout of radiation images recorded by radiation imaging can be improved.

Further, because readout of the radiation image from the detecting panel is performed repeatedly for each imaging operation, a great advantageous effect can be exhibited with regard to the improvement in readout efficiency. That is, because the temporal intervals among each of a plurality of imaging operations which are performed repeatedly can be shortened, the amount of time between the initiation and completion of sequential imaging can be shortened. In the case that the subject is a portion of a patient, the breast of the patient for example, the burden on the patient during the imaging process can be lightened. In addition, motion artifacts that occur within radiation images can be decreased, and radiation images having higher image quality can be obtained.

A configuration may be adopted, wherein the high speed readout means administers a binning process on image signals recorded in detection pixels other than those within the necessary readout region prior to reading out the image signals. Alternatively, a configuration may be adopted, wherein the high speed readout means discards image signals recorded in detection pixels other than those within the necessary readout region via a clear line provided to remove electric signals which are accumulated in the detection pixels of the detecting panel. As a further alternative, a configuration may be adopted, wherein the high speed readout means reads out image signals recorded in detection pixels other than those within the necessary readout region at a higher readout clock signal frequency, which regulates the timing of the readout process. In all of these cases, the speed at which the image signals are read out from regions other than the necessary readout region can be made faster than the speed at which the image signals are read out from the necessary readout region.

A configuration may be adopted, wherein the setting section determines the necessary readout region according to the open state of a irradiation field aperture that determines the radiation field of the radiation during imaging. In this case, the necessary readout region can be determined more positively.

A configuration may be adopted, wherein the radiation source emits radiation at a normal dosage, and radiation at a lower dosage than the normal dosage; and the setting section may determine the necessary readout region employing a radiation image which is recorded on the detecting panel by imaging with the lower dosage radiation. In this case, the necessary readout region can be determined more positively.

A configuration may be adopted, wherein the first and second radiation CT apparatuses of the present invention further comprises a visible light imaging means for performing visible light imaging that converts the propagating region of radiation, which is emitted from the radiation source and detected by the detecting panel, to the visible range; and wherein the setting section sets the necessary readout region employing visible light images, which are obtained by visible light imaging by the visible light imaging means. In this case, the necessary readout region can be determined more positively.

BEST MODE FOR CARRYING OUT THE INVENTION

Figure 1:
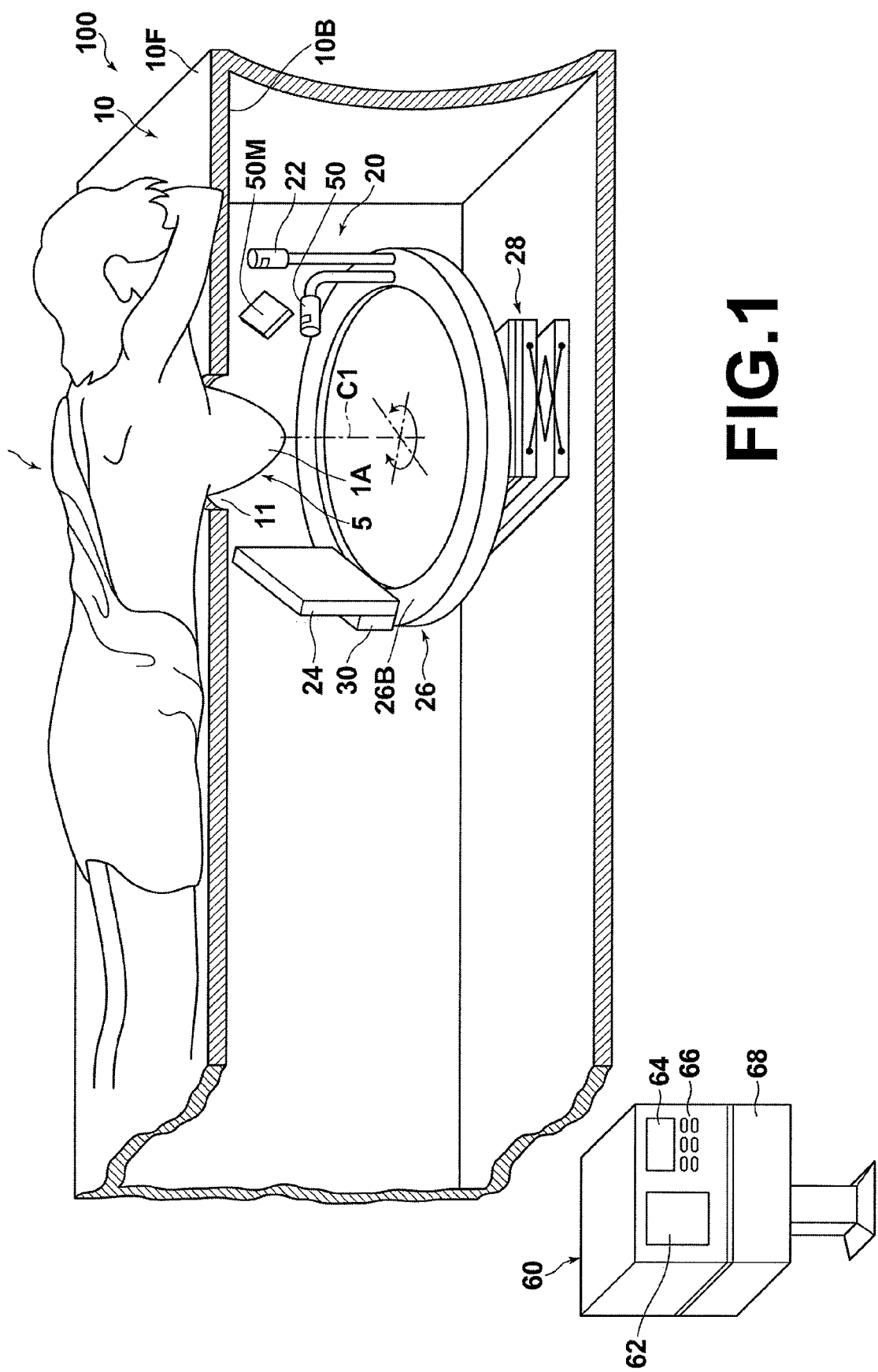
FIG. 1 is a perspective view that illustrates the schematic construction of an example of a radiation CT apparatus according to an embodiment of the present invention.
Figure 2:
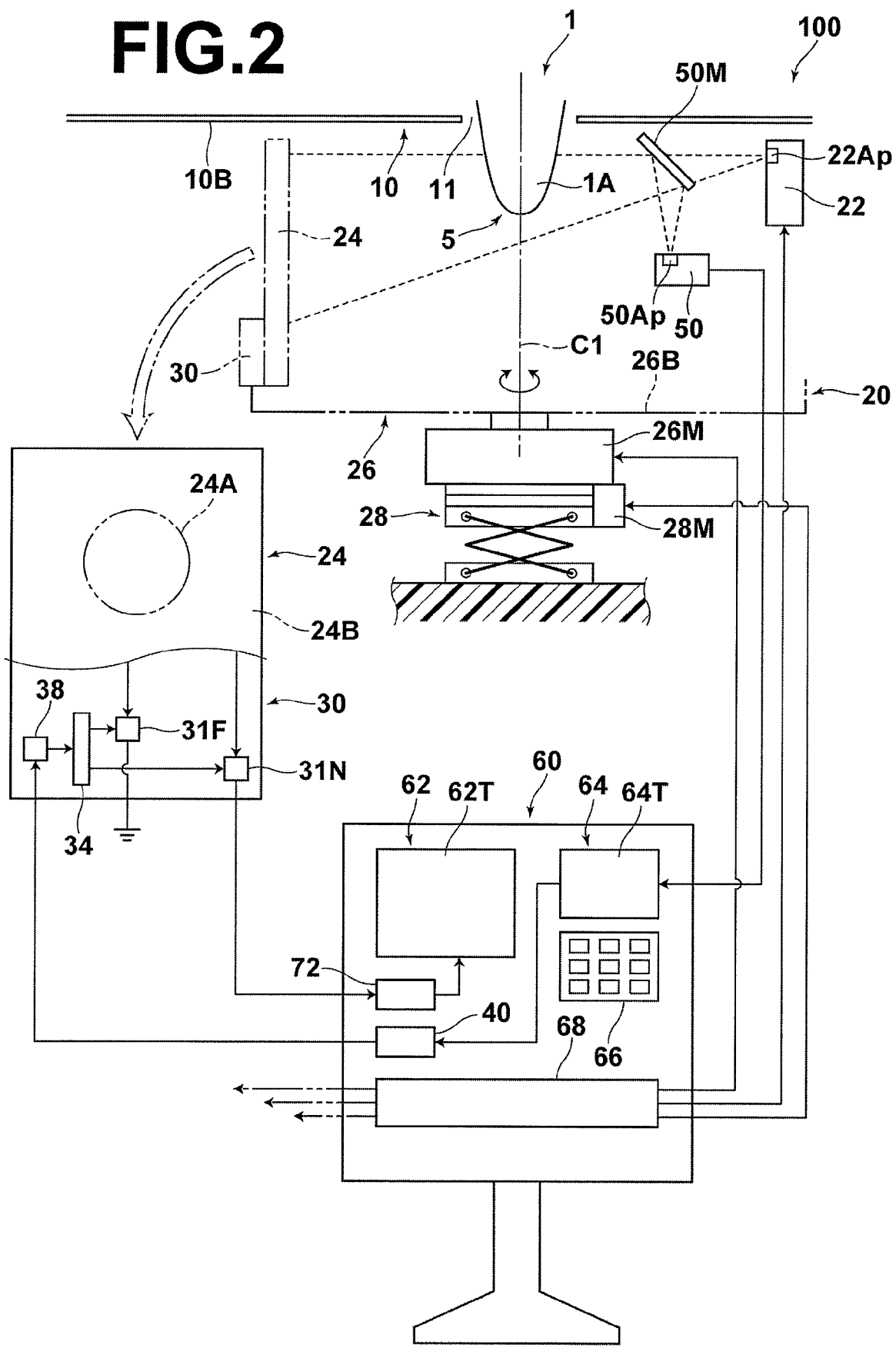
FIG. 2 is a block diagram for explaining the operation of the radiation CT apparatus of FIG. 1.
Figure 3:
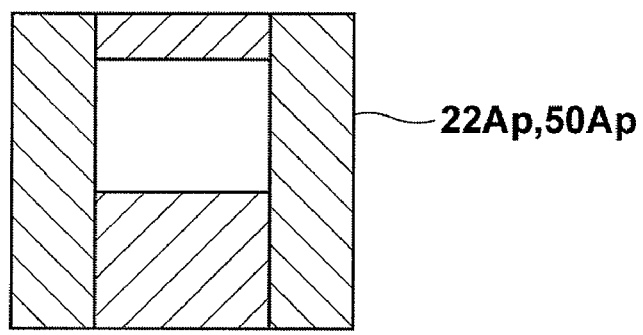
FIG. 3 is a diagram that illustrates a irradiation field aperture provided in the radiation CT apparatus of FIG. 1.

Hereinafter, embodiments of the present invention will be described with reference to the attached drawings. FIG. 1 is a perspective view that illustrates the schematic construction of an example of a radiation CT apparatus 100 according to an embodiment of the present invention. FIG. 2 is a block diagram for explaining the operation of the radiation CT apparatus 100 of FIG. 1. FIG. 3 is a diagram that illustrates a irradiation field aperture provided in the radiation CT apparatus 100 of FIG. 1.

The radiation CT apparatus 100 illustrated in FIG. 1 is equipped with: a bed portion 10 for supporting a patient 1, in which an opening 11 through which the breast 1A of the patient 1 is to pass through is formed; an imaging section 20 that performs radiation imaging; and a readout section 30 that reads out radiation images recorded by the imaging section 20.

The imaging section 20 includes: a radiation source 22 that emits radiation in a conical manner (hereinafter, also referred to as "conical radiation"), a detecting panel 24 for detecting the radiation emitted by the radiation source 22; and a rotating section 26 for integrally rotating the radiation source 22 and the detecting panel 24 about an axis of rotation C1. The imaging section 20 is capable of being rotated 360° about the axis of rotation C1.

The radiation source 22 and the detecting panel 24 are provided facing each other with the axis of rotation C1 that passes through the breast 1A, which is placed at a predetermined position 5 through the opening 11, therebetween. Note that the predetermined position 5 is the position at which a subject is placed during radiation imaging. Here, the predetermined position 5 is the position at which the breast 1A, which is the subject of radiation imaging, is placed through the opening 11.

The axis of rotation C1, the radiation source 22, and the detecting panel 24 are provided on a rotating plate 26B of the rotating section 26, and the positional relationships among these components are fixed. A detecting surface, in which detection pixels that constitute the detecting panel 24 are arranged, may be a planar surface or a curved surface.

The imaging section 20 is provided at the underside 10B of the bed portion 10, opposite the upper side 10F that supports the patient 1.

The readout section 30 reads out electrical image signals that represent radiation images, which are recorded in the detection panels that constitute the detecting panel 24 when they are irradiated with radiation which has passed through the breast 1A.

In the radiation CT apparatus 100, conical radiation is emitted from the radiation source 22, passes through the breast 1A, and irradiated onto the detecting panel 22 while the radiation source 2 and the detecting panel 24 are integrally rotated about the axis of rotation that passes through the opening 11, formed in the bed portion 10 for supporting the patient. The radiation image which is recorded in the detecting panel 22 is read out. The above steps are repeated a plurality of times, and radiation images that represent the breast 1A are sequentially obtained. That is, the readout section 30 reads out the image signals recorded in the detection pixels of the detecting panel 24 for each imaging operation of the sequential imaging operations.

Further, the radiation CT apparatus is equipped with a setting section 40, for setting a necessary readout region 24A, which is a region constituted by pixels for which readout is necessary.

The readout section 30 is equipped with: a normal readout section 31N for reading out image signals recorded in the detection pixels that constitute the detecting panel 24 at a normal speed; a high speed readout section 31F for reading out image signals recorded in the detection pixels that constitute the detecting panel 24 at a high speed; a readout switching section 34 for switching between readout of the image signals by the normal readout section 31N and readout of the image signals by the high speed readout section 31F; and a readout control section 38 for referring to the results of setting by the setting section 40 and controlling the readout switching means 34 such that image signals recorded in detection pixels within the necessary readout region 24A are read out by the normal readout section 31N, and image signals recorded in detection pixels in unnecessary regions 24B outside the necessary readout region 24A are read out by the high speed readout section 31F.

Accordingly, the amount of time required for readout by the high speed readout section 31F is shorter than the amount of time required for readout by the normal readout section 31N. That is, the amount of time between readout of image signals from a specific detection pixel to initiation of readout of image signals from a next detection pixel is shorter during readout performed by the high speed readout section 31F, compared to readout performed by the normal readout section 31N.

The high speed readout section 31F may perform a binning process on image signals recorded in detection pixels other than those within the necessary readout region 24A prior to reading out the image signals. Alternatively, the high speed readout section 31F may discard image signals recorded in detection pixels other than those within the necessary readout region 24A via a clear line provided to remove electric signals which are accumulated in the detection pixels of the detecting panel 24. As a further alternative, the high speed readout section 31F may read out image signals recorded in detection pixels other than those within the necessary readout region 24A at a higher readout clock signal frequency, which regulates the timing of the readout process. Note that as the number of detection pixels which are subject to a single binning process is increased, the more the readout time for image signals per each detection signal can be shortened.

An irradiation field aperture 22Ap (also referred to as a collimator) as illustrated in FIG. 3 is provided in front of the radiation source 22. The irradiation field of the radiation emitted from the radiation source 22 is adjusted by the irradiation field aperture 22Ap. If the irradiation field aperture 22A is narrowed, the amount of scattered X-rays decreases, and radiation images of higher image quality can be obtained.

Further, the radiation CT apparatus 100 is equipped with a visible light imaging section 50 for performing visible light imaging that converts the propagating region of radiation, which is emitted from the radiation source 22 and detected by the detecting panel 24, to the visible range. An optical image that represents the breast 1A, or an optical image that represents the detecting panel 24, is focused on and imaged by the visible light imaging section 50 via a mirror 50M. Here, the light receiving section of the visible light imaging section 50 has a conjugate optical relationship with the radiation emission point of the radiation source 22.

The mirror 50M transmits radiation. Therefore, it is not necessary to remove the mirror 50M from the propagating region of the radiation during radiation imaging. However, it is desirable to remove the mirror 50M from the propagating region of the radiation in the case that radiation images having high image quality are desired.

Note that an aperture 50Ap as illustrated in FIG. 3 is provided in front of the visible light imaging section 50, in a manner similar to the irradiation field aperture 22Ap of the radiation source 22. The irradiation field aperture 22Ap and the aperture 50Ap are synchronized under control of a controller 68 to be described later, such that the propagating region of the radiation emitted by the radiation source 22 and detected by the detecting panel 24 and the visual field range of the visible light imaging section 50 are always matched.

Note that the degree to which the irradiation field aperture 22Ap and the aperture 50Ap are opened may be determined either automatically or manually.

Note that the visible light imaging section 50 is fixed on the rotating plate 26B, and the positional relationship thereof with respect to the radiation source 22 is fixed. Accordingly, the visible light imaging section 50, the radiation source 22, and the detecting panel 24 are integrally rotated about the axis of rotation C1 by a motor 26M of the rotating section 26.

The rotating section 26 is provided on an XYZ table 28. Therefore, the entirety of the imaging section 20 is movable in the direction of the axis of rotation C1 (the Z direction) as well as the directions perpendicular to the axis of rotation C1 (the X and Y directions) by movement of the XYZ table 28. The XYZ table 28 is constituted by known linear slide guides and the like, and is driven by a plurality of motors 28M.

Note that a console 60, which is provided in the vicinity of the radiation CT apparatus 100, includes: a radiation image display section 62 for displaying radiation images represented by the image signals read out from the detecting panel 24; a visible light image display section 64 for displaying visible light images obtained by visible light imaging by the visible light imaging section 50 in real time; an operating section 66 for performing various input operations; and the controller 68 for controlling the operations of the entire apparatus and the timing of each of the operations.

Note that pressure sensitive touch panels, which are integrated with display screens, are provided in the radiation image display section 62 and the visible light image display section 64. Specific regions within displayed images can be directly specified by employing the touch panels, for example.

Hereinafter, the operation of the radiation CT apparatus 100 will be described.

Figure 4:
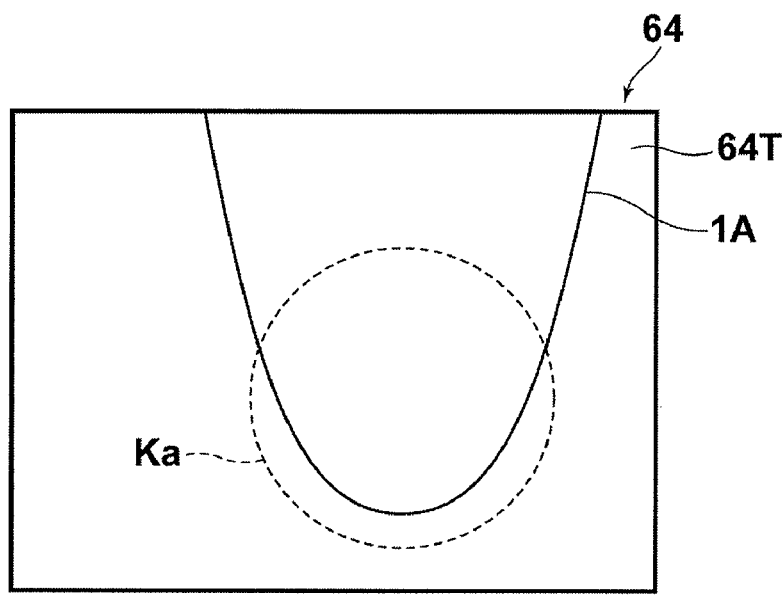
FIG. 4 is a diagram that illustrates how an image displayed by a visible light image display section is utilized to specify the range of a necessary readout region.

FIG. 4 is a diagram that illustrates how an image displayed by the visible light image display section is utilized to specify the range of a necessary readout region 24A.

The patient lies face down on the bed portion 10, passes her breast 1A through the opening 11 of the bed portion 10, and places her breast 1A at the predetermined position.

The operating section 66 is operated to cause a visible light image to be displayed by the visible light image display section 64. Here, the imaging range of the visible light image that represents the breast 1A displayed by the visible light image display section 64 and the imaging range of a radiation image that represents the breast 1A obtained by radiation imaging match.

Next, the range of a necessary readout region 24A within the detecting panel 24 is specified. Here, the touch panel 64T, which is integrally provided on the display screen of the visible light image display section 64, is employed to specify a region of interest within the breast 1A displayed by the visible light imaging display section 64.

As illustrated in FIG. 4, a pen draws a region on the touch panel 64T that surrounds a region of interest Ka within the breast 1A displayed by the visible light image display section 64.

The necessary readout range specified as described above is input to the setting section 40. The setting section 40 sets a region within the detecting panel 24, at which a radiation image of the necessary readout range (the region of interest Ka within the breast 1A) is to be formed, as the necessary readout region 24A. At the same time, regions of the detecting panel 24 other than the necessary readout region 24A are set to be unnecessary regions 24B.

Next, a first radiation imaging operation of the breast 1A is performed by the imaging section 20 according to an operation of the operating section 66. Thereby, a radiation image that represents the breast 1A is recorded in the detecting panel 24.

The readout control section 38 refers to the setting results, which are stored in the setting section 40. Then, the readout control section 38 controls the readout switching section 34 such that image signals recorded in detection pixels within the necessary readout region 24A are read out by the normal readout section 31N, and image signals recorded in detection pixels within the unnecessary regions 24B are read out by the high speed readout section 31F.

The normal readout section 31N reads out the image signals which are recorded in the detection pixels within the necessary readout region 24A, and outputs the image signals to an image processing section 72 of the console.

On the other hand, the high speed readout section 31F administers binning processes on the image signals which are recorded in the detection pixels within the unnecessary regions 24B, leads these image signals to a clear line, or reads these image signals with the frequency of a readout clock signal set to be higher than that during readout by the normal readout section 31N. Thereafter, the high speed readout section 31F removes these image signals by grounding (to earth) them or the like, without outputting these image signals to the image processing section 72.

The image processing section 72 stores the image signals input thereto from the normal readout section 31N.

When all of the image signals recorded in the detecting panel 24 are read out by the readout section 30, the detecting panel 24 is in a state in which a next radiation imaging operation is possible. At this point in time, a second radiation imaging operation is executed by the imaging section 20, and the processes described are repeated. Thereby, image signals output from the normal readout section 31N are accumulated in the image processing section 72.

Thereafter, radiation imaging operations by the imaging section 20 and readout of image signals by the readout section 30 are repeatedly executed, and the sequential imaging of the breast 1A is completed.

Note that the necessary readout region 24A and the unnecessary regions 24B, which are stored in the setting section 40 at the first radiation imaging operation, are employed during readout of image signals from the detecting panel 24 in the second and subsequent radiation imaging operations.

Accordingly, it is desirable for the imaging section 20 to be moved by the XYZ table 28 such that the axis of rotation C1 passes through the center of the region of interest Ka within the breast 1A prior to the first radiation imaging operation. This positional adjustment enables displacement of the position of the region of interest Ka with respect to the irradiation field of radiation, which moves during the sequential imaging operations, to be suppressed. Thereby, the region of interest Ka can be maintained at the center of the irradiation field.

When the sequential imaging operations are completed, the image signals that represent each of the radiation images, which have been read out from the detecting panel 24 for each radiation imaging operation, are accumulated in the image processing section 72. The image processing section 72 reconstitutes the image signals that represent each of the radiation images, to generate image signals that represent a radiation CT image. The image signals that represent the radiation CT image are input to the radiation image display section 62, and the radiation image display section 62 displays the radiation CT image.

As described above, the radiation CT apparatus 100 is capable of shortening the amount of time required to read out radiation images. That is, readout efficiency can be improved, and the amount of time required for sequential imaging of radiation images can be shortened.

Note that the necessary readout region 24A may be changed for each imaging operation. In this case, it is desirable for the setting of the necessary readout region 24A to be performed automatically. An example of a method for performing automatic setting of the necessary readout region 24A is that in which a region of interest is automatically extracted from an image of the breast 1A, which is displayed by the visible light image display section 64, by image processes.

In the embodiment described above, the setting section 40 determined the necessary readout region 24A by a region being specified on the touch panel 64T of the visible light image display section 64. However, the present invention is not limited to such a configuration, and the necessary readout region 24A may be determined by various other methods.

Figure 5:
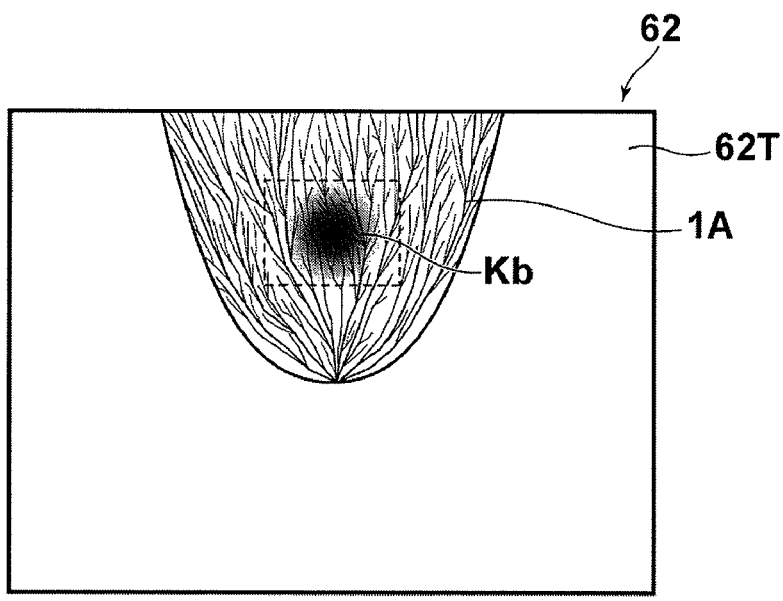
FIG. 5 is a diagram that illustrates how an image displayed by a radiation image display section is utilized to specify the range of a necessary readout region.

For example, the radiation source 22 may be configured to emit radiation at a normal dosage, and radiation at a lower dosage than the normal dosage. A radiation image, which is recorded in the detecting panel 24 by radiation imaging using the lower dosage radiation, may be read out by the normal readout section 31N. The read out radiation image may be displayed by the radiation image display section 62, and a touch panel 62T, which is provided in the radiation image display section 62, may be employed to specify a region for the setting section 40 to determine the necessary readout region, in a manner similar to the embodiment described above. If this configuration is adopted, the necessary readout region 24A may be set such that radiation images that include a diseased region Kb within the breast 1A as illustrated in FIG. 5, which is not displayed by the visible light image display section 64, are read out.

As another alternative, the open state of the irradiation field aperture 22Ap may be detected by the controller 68. Then, the setting section 40 may set the necessary readout region 24 to be a region of the detecting panel 24 onto which radiation is to be irradiated according to the open state of the irradiation field aperture 22Ap. In this case, A visible light image that represents an region equivalent to the irradiation field is displayed by the visible light image display section 64. Therefore, the region which is the target of radiation imaging, corresponding to the radiation image formed in the necessary readout region 24A, can be easily recognized.

Note that the detecting panel 24 is that which records a two dimensional radiation image that represents the entirety of a subject when it receives a single irradiation of radiation which has passed through the subject. In addition, it is desirable for the imaging section to not be moved in the direction of the axis of rotation during radiation CT imaging. Further, it is desirable for the imaging section to not be moved in the directions perpendicular to the axis of rotation during radiation CT imaging.

Note that the subject of radiation imaging operations is not limited to breasts, and may be limbs or the thoracic region of a patient.

In the sequential radiation imaging described above, it is desirable for the timing of each radiation imaging operation to be synchronized with respiration or heart rate. By adopting this configuration, motion artifacts in the radiation images obtained by radiation imaging operations can be reduced, and the image quality thereof can be improved. That is, the shorter the amount of time required for sequential imaging of radiation images, more imaging operations can be performed during the time in which a patient is holding their breath and lying still. Accordingly, the occurrence of motion artifacts can be reduced.

Figure 6:
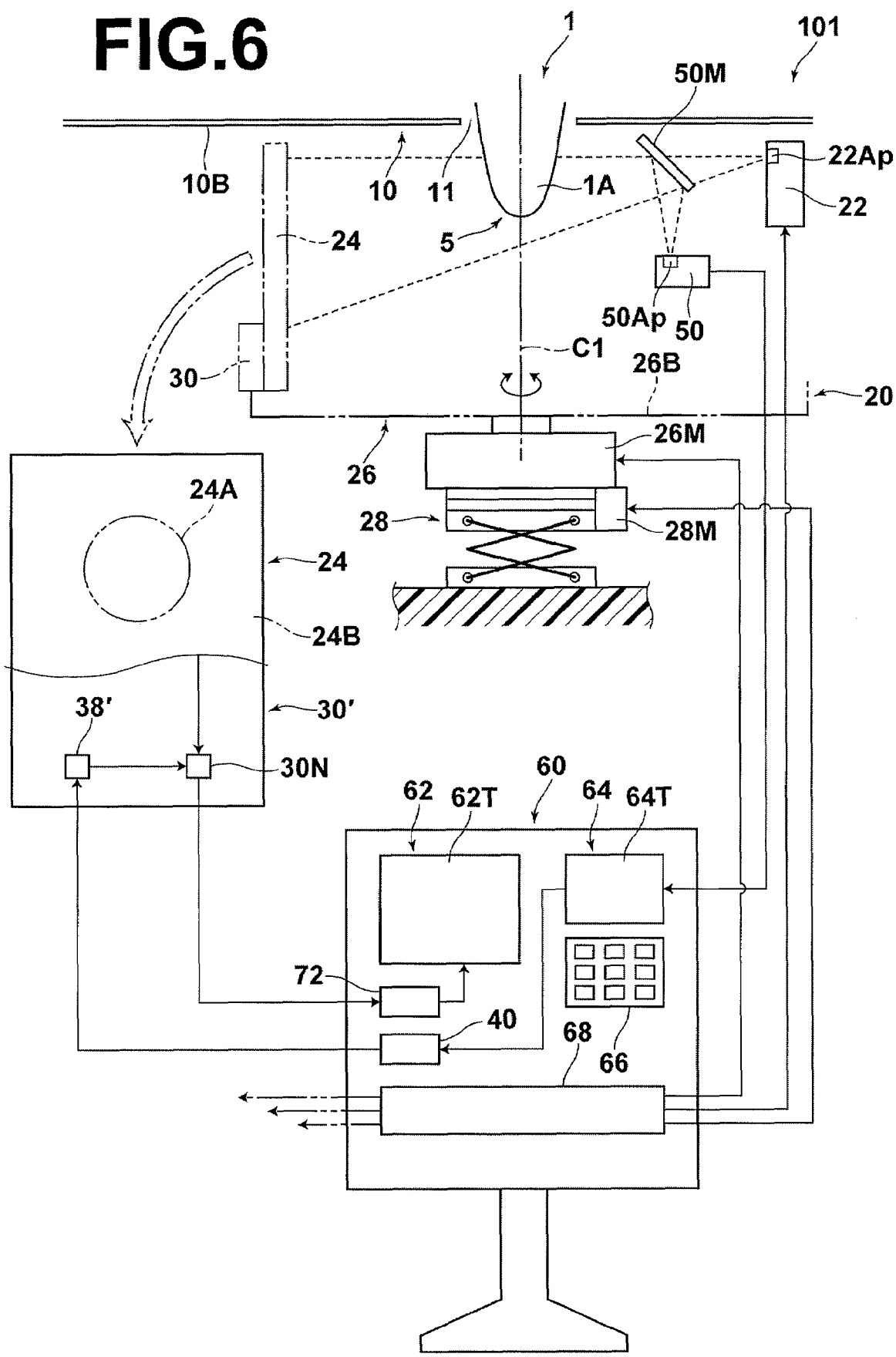
FIG. 6 is a diagram that illustrates a radiation CT apparatus according to an alternate embodiment of the present invention.

Next, an alternate embodiment of the radiation CT apparatus 100 will be described. FIG. 6 is a diagram that illustrates a radiation CT apparatus 101 according to the alternate embodiment of the present invention. The radiation CT apparatus 101 differs from the radiation CT apparatus 100 only in the configuration of a readout section 30', and all other components and operations are the same as those of the radiation CT apparatus 100. Note that in FIG. 6, the same reference numerals are employed to denote components of the radiation CT apparatus 101 which are the same as those of the radiation CT apparatus 100.

The readout section 30' of the radiation CT apparatus is equipped with: a normal readout section 31N for reading out image signals recorded in the detection pixels that constitute the detecting panel 24 at a normal speed; and a control section 38' for referring to the results of setting by a setting means 40 and controlling the normal readout section 31N such that only image signals recorded in detection pixels within a necessary readout region are read out.

The setting section 40 sets the necessary readout region 24A and the unnecessary regions 24B in the same manner as in the first embodiment described above. Then, the readout control section 38' refers to the results of setting by the setting section 40, and controls the normal readout section 31N such that only image signals recorded in detection pixels within the necessary readout region 24A are read out. Note that readout is not performed with respect to the unnecessary regions 24B, which are regions of the detecting panel 24 other than the necessary readout region 24A. Accordingly, image signals are repeatedly recorded by the radiation irradiated during each radiation imaging operation and accumulate in the detection pixels within the unnecessary regions 24B. However, these image signals are not utilized.

The normal readout section 31N sequentially outputs the read out image signals to an image processing section 72 of a console 60. The image processing section 72 sequentially generates radiation images employing the image signals input thereto. When sequential radiation imaging is completed, the image processing section reconstitutes the radiation images to generate a radiation CT image. The radiation CT image is displayed by the radiation image display section 62.

As described above, readout efficiency during readout of radiation images can also be improved by the radiation CY apparatus 101. This decreases the burden placed on the apparatus, and enables the amount of time required for sequential imaging of radiation images to be shortened.

Note that the various components related to the radiation CT apparatus 100 other than the readout section 30', such as the radiation source, the detecting panel, the rotating section, the visible light imaging section, the XYZ stage, the controller, the console, and the like, may also be employed by the radiation CT apparatus 101.

Hereinafter, information to complement the contents of this specification will be listed. Note that a portion of the information below will overlap the contents of this specification.

Breasts are of various sizes, and therefore, it is desirable for total imaging time not to be uniform for all patients. It is desired for total imaging time to be shortened to prevent motion artifacts from appearing in radiation images, because breasts are in the proximity of the lungs and the heart.

Conventional imaging operations require ten seconds for an imaging section to complete a single rotation about an axis of rotation.

It is desirable for image signals of regions other than those that represent the region of an imaging target to undergo binning processes, or to not be read out.

It is desirable for different readout processes to be administered according to the open state (wide or narrow) of a collimator (irradiation field aperture) even within the region of an imaging target.

It is common for the open state of collimators to be determined by user input.

The present invention may be applied to cases in which the opening size of a collimator (the area of the detecting panel which is irradiated by radiation) is greater than the size of a breast, and cases in which the opening size of a collimator is less than the size of a breast. That is, there are cases in which the necessary readout region is set such that a radiation image that represents an entire breast is included therein, and cases in which the necessary readout region is set such that a radiation image that represents a portion of a breast is included therein.

It is desirable for the timing of each radiation imaging operation within sequential radiation imaging operations to be synchronized with the movement of the heart and lungs.

Taking the fact that breasts are shaped asymmetrically, the size of the necessary readout region within the detecting panel may be changed dynamically, based on the visible light images, which are being displayed in real time (or based on an immediately preceding image).

The present invention is not limited to radiation CT imaging of breasts. The present invention may also be applied to cone beam radiation CT apparatuses (radiation CT apparatuses having flat panel sensors, onto which X-rays having a conical distribution are irradiated to perform radiation imaging) which are utilized in cases that the subjects of radiation imaging are thoracic regions and limbs. Note that in common radiation CT apparatuses, radiation emitted from radiation sources have linear X-ray distributions, which are received by linear sensors.

What is claimed is:

1. A radiation CT apparatus, comprising:
an imaging portion constituted by a radiation source that emits radiation in a conical manner, a detecting panel for detecting the radiation, the radiation source and the detecting panel being provided to face each other with an axis of rotation that passes though a predetermined position sandwiched therebetween, and rotating means for integrally rotating the radiation source and the detecting panel about the axis of rotation; and
readout means for reading out image signals which are recorded in detection pixels that constitute the detecting panel;
the imaging portion continuously imaging a subject which is placed at the predetermined position while rotating the radiation source and the detecting panel about the axis of rotation, and the image signals being read out for each imaging operation by the readout means; further comprising:
setting means for setting a necessary readout region within the detecting panel; and
control means for referring to the results of setting by the setting means and controlling the readout means such that only image signals recorded in detection pixels within the necessary readout region are read out.

2. A radiation CT apparatus as defined in claim 1, wherein:
the setting section determines the necessary readout region according to the open state of a irradiation field aperture that determines the radiation field of the radiation during imaging.

3. A radiation CT apparatus as defined in claim 1, wherein:
the radiation source emits radiation at a normal dosage, and radiation at a lower dosage than the normal dosage; and
the setting section determines the necessary readout region employing a radiation image which is recorded on the detecting panel by imaging with the lower dosage radiation.

4. A radiation CT apparatus as defined in claim 1, further comprising:
a visible light imaging means for performing visible light imaging that converts the propagating region of radiation, which is emitted from the radiation source and detected by the detecting panel, to the visible range; and wherein the setting section sets the necessary readout region employing visible light images, which are obtained by visible light imaging by the visible light imaging means.

5. A radiation CT apparatus as defined in claim 1, wherein: the setting section sets the necessary readout region for each imaging operation of the sequential imaging operations performed by the imaging section.

6. A radiation CT apparatus as defined in claim 5, wherein: the setting section sets the necessary readout region for each imaging operation of the sequential imaging operations performed by the imaging section, employing a radiation image obtained by a previous radiation imaging operation.

7. A radiation CT apparatus, comprising:
an imaging portion constituted by a radiation source that emits radiation in a conical manner, a detecting panel for detecting the radiation, the radiation source and the detecting panel being provided to face each other with an axis of rotation that passes though a predetermined position sandwiched therebetween, and rotating means for integrally rotating the radiation source and the detecting panel about the axis of rotation; and
readout means for reading out image signals which are recorded in detection pixels that constitute the detecting panel;
the imaging portion continuously imaging a subject which is placed at the predetermined position while rotating the radiation source and the detecting panel about the axis of rotation, and the image signals being read out for each imaging operation by the readout means; further comprising:
setting means for setting a necessary readout region within the detecting panel;
normal readout means for reading out image signals recorded in the detection pixels that constitute the detecting panel at a normal speed;
high speed readout means for reading out image signals recorded in the detection pixels that constitute the detecting panel at a high speed;
readout switching means for switching between readout of the image signals by the normal readout means and readout of the image signals by the high speed readout means; and
control means for referring to the results of setting by the setting means and controlling the readout switching means such that image signals recorded in detection pixels within the necessary readout region are read out by the normal readout means, and image signals recorded in detection pixels other than those within the necessary readout region are read out by the high speed readout means.

8. A radiation CT apparatus as defined in claim 7, wherein: the high speed readout means performs a binning process on image signals recorded in detection pixels other than those within the necessary readout region prior to reading out the image signals.

9. A radiation CT apparatus as defined in claim 7, wherein: the high speed readout means discards image signals recorded in detection pixels other than those within the necessary readout region via a clear line provided to remove electric signals which are accumulated in the detection pixels of the detecting panel.

10. A radiation CT apparatus as defined in claim 7, wherein:
the high speed readout means reads out image signals recorded in detection pixels other than those within the necessary readout region at a higher readout clock signal frequency, which regulates the timing of the readout process.

11. A radiation CT apparatus as defined in claim 7, wherein:
the setting section determines the necessary readout region according to the open state of a irradiation field aperture that determines the radiation field of the radiation during imaging.

12. A radiation CT apparatus as defined in claim 7, wherein:
the radiation source emits radiation at a normal dosage, and radiation at a lower dosage than the normal dosage; and
the setting section determines the necessary readout region employing a radiation image which is recorded on the detecting panel by imaging with the lower dosage radiation.

13. A radiation CT apparatus as defined in claim 7, further comprising:
a visible light imaging means for performing visible light imaging that converts the propagating region of radiation, which is emitted from the radiation source and detected by the detecting panel, to the visible range; and
wherein
the setting section sets the necessary readout region employing visible light images, which are obtained by visible light imaging by the visible light imaging means.

14. A radiation CT apparatus as defined in claim 7, wherein:
the setting section sets the necessary readout region for each imaging operation of the sequential imaging operations performed by the imaging section.

15. A radiation CT apparatus as defined in claim 14, wherein:
the setting section sets the necessary readout region for each imaging operation of the sequential imaging operations performed by the imaging section, employing a radiation image obtained by a previous radiation imaging operation.

16. A radiation CT apparatus as defined in claim 15, wherein:
the previous radiation imaging operation is the immediately preceding radiation imaging operation.

17. A radiation CT apparatus as defined in claim 7, wherein:
the necessary readout region is a region within the detecting panel at which a radiation image of the subject is formed by the radiation imaging operation.

18. A radiation CT apparatus as defined in claim 7, wherein:
the necessary readout region is a region within the detecting panel at which a radiation image that represents a region of interest within the subject is formed by the radiation imaging operation.

19. A radiation CT apparatus as defined in claim 7, wherein:
the subject is a breast.

20. A radiation CT apparatus as defined in claim 18, wherein:
the region of interest is a diseased area.

* * * * *